United States Patent
Rice et al.

(10) Patent No.: US 9,295,745 B2
(45) Date of Patent: Mar. 29, 2016

(54) METHOD FOR CONSTRUCTING A DIVERSITY INDEX AND A VIABILITY INDEX OF MICROORGANISMS IN PROCESS SAMPLES

(75) Inventors: Laura E. Rice, St. Charles, IL (US); Liliya Lund, Warrenville, IL (US)

(73) Assignee: NALCO COMPANY, Naperville, IL (US)

(*) Notice: Subject to any disclaimer, the term of this patent is extended or adjusted under 35 U.S.C. 154(b) by 793 days.

(21) Appl. No.: 13/550,748

(22) Filed: Jul. 17, 2012

(65) Prior Publication Data

US 2013/0189152 A1    Jul. 25, 2013

Related U.S. Application Data

(63) Continuation-in-part of application No. 13/374,949, filed on Jan. 24, 2012, now Pat. No. 8,613,837.

(51) Int. Cl.
- *A61L 2/16* (2006.01)
- *A61L 2/24* (2006.01)
- *C12Q 1/68* (2006.01)

(52) U.S. Cl.
CPC ............... *A61L 2/24* (2013.01); *A61L 2202/14* (2013.01); *C12Q 1/689* (2013.01)

(58) Field of Classification Search
CPC .................................................. A61L 2/16
USPC ............................................................ 422/3
See application file for complete search history.

(56) References Cited

U.S. PATENT DOCUMENTS

| | | | |
|---|---|---|---|
| 5,190,728 | A | 3/1993 | Robertson et al. |
| 5,282,537 | A | 2/1994 | Wong |
| 5,698,412 | A | 12/1997 | Lee et al. |
| 5,856,119 | A | 1/1999 | Lee et al. |
| 5,928,875 | A | 7/1999 | Breen et al. |
| 7,018,793 | B1 | 3/2006 | Short |
| 2002/0031771 | A1 | 3/2002 | Short |
| 2007/0134649 | A1 | 6/2007 | Kolari et al. |

FOREIGN PATENT DOCUMENTS

| | | |
|---|---|---|
| CA | 2524086 A1 | 4/2007 |
| JP | 2003-164281 A | 6/2003 |
| JP | 2006-217869 A | 8/2006 |

(Continued)

OTHER PUBLICATIONS

English language machine translation of JP 2006217869 A; Aug. 2006; inventor: Iiizumi.*

(Continued)

*Primary Examiner* — Sean E Conley
(74) *Attorney, Agent, or Firm* — Benjamin E. Carlsen

(57) ABSTRACT

The invention is directed towards methods and compositions for identifying the specific microorganisms present in a particular portion of a papermaking processes. The method involves obtaining and comparing a diversity index of a sample from the process. Because no system is completely free from biological infestation, utilizing information taken from the changes in the populations provides information useful in protecting the system from unwanted effects. Not only does the diversity index allow for the distinguishing between biological and non-biological events, it even allows for the prediction of problems without previously knowing that a particular organism will cause a particular problem.

15 Claims, 4 Drawing Sheets

A Total Bacteria

B Primary Biofilm-Formers

C Adaptive Biofilm-Formers

(56) References Cited

FOREIGN PATENT DOCUMENTS

| JP | 2006217869 A | * | 8/2006 |
|---|---|---|---|
| WO | 2004042082 A1 | | 5/2004 |
| WO | 2013112656 A1 | | 8/2013 |

OTHER PUBLICATIONS

Randall Saiki et al., Article Primer Directed Enzymatic Amplificiation of DNA with a Thermostable DNA Polymerase, Science, vol. 239, pp. 487-491 (1988).
Kary Mullis et al., Article Specific Synthesis of DNA in Vitro via a Polymerase-Catalyzed Chain Reaction, Methods in Enzymology, vol. 155, pp. 335-350 (1987).
Zhang et al., Identifying Poneer bacterial species responsible for befouling membrane bioreactors, Environmental Microbiology, vol. 8, No. 3., pp. 433-440 (2006).
International Search Report mailed Oct. 16, 2012 for related PCT International Application No. PCT/US2013/050896.
Piasecka et al, "Anaysis of the microbial community structure in a membrane bioreactor during initial stages of iltration", The Journal of Bioadhesion and Biofilm Research, 16 pages, Published online Feb. 21, 2012.
Peltola et al., "Quantitative contributions of bacteria and of Deinococcus geothermalis to deposits and slimes in paper ndustry", J Ind Microbial Biotechnol, ppgs 1651-1657, published online Aug. 26, 2008.
European Patent Office. "Partial Supplementary European Search Report", issued in connection to International Application No. 13819640.7, issued on Jan. 22, 2016.

* cited by examiner

Mill 1: Machine felt
- % Adaptive Biofilm-Formers
- % Primary Biofilm-Formers
- % Other Mill 2: Pickup felt
- % Adaptive Biofilm-Formers
- % Primary Biofilm-Formers
- % Other Mill 3: Pickup felt
- % Adaptive Biofilm-Former
- % Primary Biofilm-Former
- Other

METHOD FOR CONSTRUCTING A DIVERSITY INDEX AND A VIABILITY INDEX OF MICROORGANISMS IN PROCESS SAMPLES

CROSS-REFERENCE TO RELATED APPLICATIONS

This Application is a continuation in part of U.S. patent application Ser. No. 13/374,949 filed on Jan. 24, 2012 now U.S. Pat. No. 8,613,837.

STATEMENT REGARDING FEDERALLY SPONSORED RESEARCH OR DEVELOPMENT

Not Applicable.

BACKGROUND OF THE INVENTION

The present invention relates generally to compositions of matter, apparatuses and methods useful in detecting, identifying, and addressing microorganisms present in commercial process systems.

The presence and growth of certain microorganism in commercial process systems is an ongoing challenge. Many of the various stages of commercial process systems contain a variety of conditions having different amounts of water, nutrients, heat, shelter, anchoring substrates, chemical conditions, and/or an absence of predators which often function as environmental niches suitable for colonization by all sorts of microorganisms. Population growth by these microorganisms often pose a number of problems including degrading process functions and fouling the end products.

One such problem is microorganism induced crust deposit formation. Crust is the accumulation on a surface of an item present in a commercial process system of a rigid solid composition comprising deposited organic and/or inorganic material. The crust can be secretions and/or colonies of microorganisms themselves. In particular crust can include or consist of the accumulation of one or more kinds of hard shelled and/or chitin bearing and/or coral organisms. Crust can have many negative impacts on systems such as decreased operational efficiency, premature equipment failure, loss in productivity, loss in product quality, and increased health-related risks. Worst of all crust must often be physically removed by scraping or other physical means and this requires expensive shut downs or disassembly of part or all of the process system.

Another problem microorganisms pose is through the formation of biofilms. Biofilms are layers of organic materials comprising microorganisms or exopolymeric substance secreted by microorganisms which aid in the formation microbial communities. Biofilms can grow on the surfaces of process equipment as well as in pools of fluid. These biofilms are complex ecosystems that establish a means for concentrating nutrients and offer protection for growth. Biofilms can accelerate crust, corrosion, and other fouling processes. Not only do biofilms contribute to reduction of system efficiencies, but they also provide an excellent environment for microbial proliferation of other microorganisms including pathogenic organisms. It is therefore important that biofilms and other fouling processes be reduced to the greatest extent possible to maximize process efficiency and minimize the health-related risks from such pathogens.

Several factors contribute to the extent of biological contamination and govern the appropriate response. Water temperature; water pH; organic and inorganic nutrients, growth conditions such as aerobic or anaerobic conditions, and in some cases the presence or absence of sunlight, etc. can play an important role. These factors also help in deciding what types of microorganisms might be present in the water system and how best to control those microorganisms. Proper identification of the microorganism is also crucial to responding appropriately. Differences regarding whether the microorganisms are plants, animals, or fungi, or if they are planktonic or sessile determines how effective various biocontrols will be. Because different microorganisms induce different problems, proper identification is crucial to properly remediating unwanted microbial effects. Finally because chemically caused problems cannot be remediated with biocides, it is also necessary to identify which problems have non-biologically based origins.

Standard techniques typically used to monitor process systems include standard plate count techniques. These techniques require lengthy incubation periods and do not provide adequate information for pro-active control and prevention of problems related to microbial growth. More recently, adenosine triphoshphate (ATP) measurements have been used as a means of pro-active control. However, the reagents are costly and small volumes are sampled from large water systems. While it is possible to quantify microbial activity in a sample with the use of the ATP assay, the reaction is unable to discriminate between ATP that is produced by one type of microorganism compared to another and it does not detect organisms that are viable but inhibited. Another disadvantage is that this method cannot be used to determine microbial contribution to sheet defects because most organisms are not viable following exposure to the heat of the dryer section. Data collection is also infrequent, leading to significant gaps in data. Therefore, this approach provides limited information on the status of microorganisms in the system of interest. In addition, these approaches are typically used to monitor planktonic bacteria. Although in some cases, surfaces might be swabbed and analyzed in order to quantify biofilm bacteria. These approaches are very tedious and time-consuming.

Dissolved oxygen (DO) probes have been used to measure microbial activity in fluids, as it is well known that microbial activity and aerobic metabolism leads to a decrease in dissolved oxygen concentrations. U.S. Pat. Nos. 5,190,728 and 5,282,537, disclose a method and apparatus for monitoring fouling in commercial waters utilizing DO measurements. However, the approach requires the use of nutrient additions to differentiate biological from non-biological fouling and there is no mention of how the probe is refreshed for further measurements after the probe surface has fouled. In addition, the approach disclosed requires a means of continuously supplying oxygen.

The standard Clark style electrochemical DC) probe has many limitations such as: chemical interferences ($H_2S$, pH, $CO_2$, $NH_3$, $SO_4$, $Cl-$, $Cl_2$, $ClO_2$, MeOH, EtOH and various ionic species), frequent calibration and membrane replacement, slow response and drifting readings, thermal shock, and high flow requirements across membranes. A new type of dissolved oxygen probe, which has recently been made commercially available by a number of companies (e.g., HACH, Loveland, Colo.), overcomes nearly all of these limitations so that DO can be measured on-line in process waters. This new DO probe (LDO) is based on lifetime fluorescence decay where the presence of oxygen shortens the fluorescence lifetime of an excited fluorophore. The fluorophore is immobilized in a film at the sensor surface and the excitation is provided with a blue LED. U.S. Pat. Nos. 5,698,412 and 5,856,119 disclose a method for monitoring and controlling biological activity in fluids in which DO is measured in combination with pH and/or ORP (oxidation-reduction potential) to measure transitions in metabolic behavior, specifically related to nutrient/substrate depletion.

Conventional plating techniques and oxidant residuals may indicate adequate biocide dosing and control of microbial growth, while deposition, defects and breaks remain prevalent. There is a clear need to provide more accurate information regarding microbial growth and biofilm formation in industrial systems. Quantitative PCR techniques allow for rapid analysis of sheet defects, felts, process water samples, etc. to determine the contribution of microorganisms to quality issues. This new approach has been demonstrated to allow for a more proactive diagnosis of problems leading to improved machine efficiency and product quality.

Thus it is clear that there is clear utility in novel methods and compositions for the proper identification of microorganisms present on in commercial process systems. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed towards a method of addressing a microorganism infestation in an industrial process system. The method comprises the steps of: 1) taking at least one first measurement which identifies the relative concentration of two or more organisms present in at least one portion of the industrial process system, the identifications at least partially defining a baseline diversity index, 2) taking at least one second measurement which identifies the relative concentration of two or more organisms present in the at least one portion of the industrial process system, the identifications at least partially defining a subsequent diversity index, the at least one second measurement taken later than the first measurement(s), 3) noting any relative change in concentration of the two organisms, 4) if the second measurement differs from the measurement by an amount greater than a pre-determined threshold amount, determining if the change is associated with an unwanted effect on the industrial process system, and 5) implementing a remedy to remediate the unwanted effect.

The first and second measurement may be performed by at least one item selected from the list consisting of DNA analysis, PCR analysis, qPCR analysis, and any combination thereof. The threshold amount may be 100 cells per ml of fluid taken from the system or 100 cells per gram of an end product of the industrial process, or other solid samples taken from the process including but not limited to felts. The method may further comprise the step of identifying if one of the organisms is a pioneer and if one is an adaptor, if one is a pioneer and its concentration increases by more than the threshold in the subsequent index, the remediation includes applying a biocide regimen targeting the pioneer, if no biofilm formers are detected the remediation includes identifying and eliminating a non-biological vector which facilitates the settlement of the microorganisms.

Regardless of the identity of the at least one organisms, if their relative concentrations increase relative to the prior measurement by an amount more than the threshold even if the overall biological population remains the same, a biocide treatment may be added to the system.

The method may further comprise the step of correlating the change in diversity index to another event that occurred in the industrial system, the other event selected from the list consisting of: changing the source of at least one feed material, changing the kind of at least one feed material, changing the rate of operating at least a portion of the system, and any combination thereof, and reversing the event. The overall concentration of cells in the sample may remain unchanged between the first and second measurements. The measurements may be taken in a portion of system that a deposit has formed on and the deposit does not contain any significant biological component. The measurements may be taken in over a plurality of locations throughout the system and the indices compare overall system populations.

At least one third diversity index measurement may be taken subsequent to the second measurement and subsequent to the remediation and the efficacy of the remediation is evaluated by the change in the relative concentrations of the at least two organisms as measured in the third diversity index measurement. The overall concentration of cells in the sample may remain unchanged between the first and second measurements, the identity of the first and second organisms are not known to cause any unwanted effects on the process equipment or end product, and an effective biocide may be added to the system to kill the first and second organisms when a threshold change is detected. One of the organisms may be capable of forming spores which are resistant to biocides and when the relative amount of that organism grows in excess of the threshold, the treatment may be targeted to the area of the process with vegetative cells to prevent sporulation.

BRIEF DESCRIPTION OF THE DRAWINGS

A detailed description of the invention is hereafter described with specific reference being made to the drawings in which:

FIG. 2 illustrates a graph of the total bacterial load of sheet defects from a coated free sheet mill (1-5), a tissue mill (6), and an uncoated free sheet mill (7) to which the invention was applied to.

FIG. 3 is a graph of the total bacterial load of sheet defect samples the invention was applied to.

DETAILED DESCRIPTION OF THE INVENTION

Figure 1:
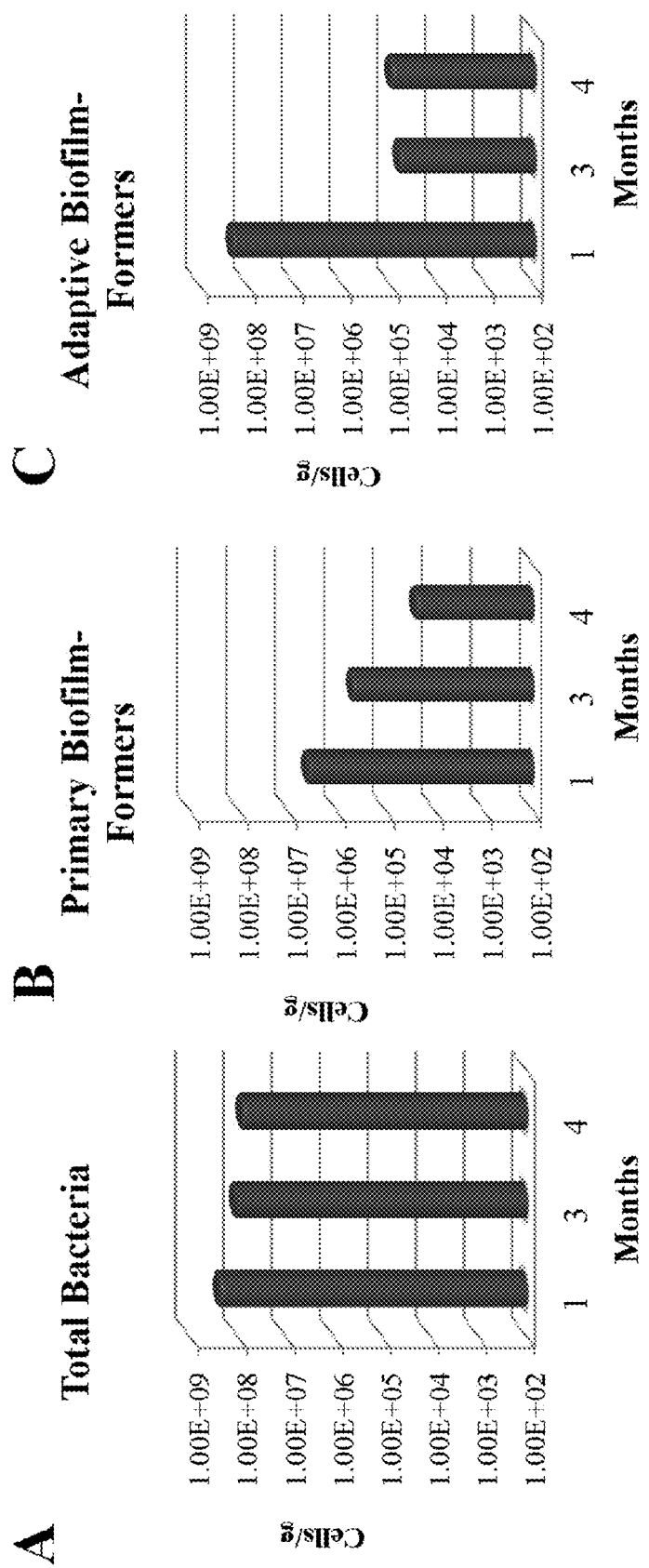
FIG. 1 contains three graphs illustrating the application of the invention for rapid detection of total bacteria (A), primary (B) and adaptive (C) biofilm-forming bacteria in headbox deposits collected at a coated free sheet mill.

The following definitions are provided to determine how terms used in this application, and in particular how the claims, are to be construed. The organization of the definitions is for convenience only and is not intended to limit any of the definitions to any particular category.

"Adaptor" means an organism that exhibits some level of tolerance to the biocontrol program. When the adaptor's microbial competition is reduced by a biocide, this adaptive organism is able to flourish and may form a biofilm.

"Biological" means a composition of matter in which at least 10% of the composition (by volume or mass) comprises cells from an organism.

"Defect" means an unwanted attribute of an item associated with an industrial process. It includes but is not limited to one or more plugs on a felt, and such attributes of paper sheet as holes, discoloration, streaks, spots, translucent spots, and any combination thereof.

"Felt" means a belt made of interweaved wool or any other fiber used in a papermaking process which functions as a conveyer of materials wherein the interweaved fibers define a plurality of lumens through which water or other fluids may pass. Felts may also provide cushioning between press rolls and may also be a medium used to remove water from papermaking materials. Felts include but are not limited to bottom felts, bottom board felts, cylinder tissue wet felts, drier felts, endless felts, pickup felts, suction pickup felts, Harper top felts, and top felts.

"Opportunist" means an organism that thrives by settling into pre-established biofilms, crusts, deposits, or other colonies of organisms, and tends to supplant, displace, or coexist alongside pioneer organisms and/or previous opportunist organisms.

"Paper Product or Paper Sheet" means any formed fibrous structure end product of a papermaking process traditionally, but not necessarily, comprising cellulose fibers. Examples of such end products include but are not limited to facial tissue, bath tissue, table napkins, copy paper, printer paper, writing paper, notebook paper, newspaper, paper board, poster paper, bond paper, cardboard, and the like.

"Papermaking Process" means one or more processes for converting raw materials into paper products and which includes but is not limited one or more of such steps as pulping, digesting, refining, drying, calandering, pressing, crepeing, dewatering, and bleaching.

"PCR Analysis" means polymerase chain reaction analysis.

"Pioneer or Primary" means an organism which attaches to a clean surface or region, thereby initiating biofilm, crust, or deposit formation at that surface.

"Plug" means a solid, semisolid, viscous, and/or other deposit of material positioned within the lumens of a felt. Plugs may inhibit the flow of material through the lumens, and/or may impair any other functionality of a felt.

"Primer" means a composition of matter, typically a short strand of nucleotides, known to be complementary to specific sections of DNA and serve as a starting point for synthesis of a nucleotide chain complementary to DNA adjacent to the specific section of DNA.

"Probe" means a composition of matter constructed and arranged to bind to a targeted section of DNA and which can be readily detected when so bound and thereby be used to indicate the presence or absence of the targeted section of DNA.

"qPCR Analysis" means quantitative polymerase chain reaction analysis.

"Microorganisms" means any organism small enough to insinuate itself within, adjacent to, on top of, or attached to equipment used in an industrial process (including papermaking), it includes but is not limited to those organisms so small that they cannot be seen without the aid of a microscope, collections or colonies of such small organisms that can be seen by the naked eye but which comprise a number of individual organisms that are too small to be seen by the naked eye, as well as one or more organisms that can be seen by the naked eye, it includes but is not limited to any organism whose presence, in some way impairs the industrial process such as forming plugs within felts and/or causing defects within paper sheets.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the Kirk-Othmer Encyclopedia of Chemical Technology, 5th Edition, (2005), (Published by Wiley, John & Sons, Inc.) this definition shall control how the term is to be defined in the claims.

At least one embodiment of the invention is directed to a method of identifying a microbiological infestation by comparing the current diversity index of at least a portion of the system to a baseline index. Virtually no commercial process system is 100% free of microbiological organisms. Process system facilities often encompass huge volumes with many inputs through which organisms can enter and contain numerous different niches for them to colonize so it always has some sort of biological population. From a commercial standpoint however it is far preferable for a system to be populated with benign organisms than to be populated with harmful organisms such as those which impair the process, damage the product, or pose dangers to people. As a result using a diversity index is a useful diagnostic approach which correlates changes in population with changes from benign effects to harmful effects. A method which correctly identifies which organisms are present and where they are, can aid in selecting the proper remedy and in deploying it in the optimal location.

A diversity index is a snapshot of the biological diversity of the organisms present in a commercial process system. Diversity indices can be system wide or can be limited to certain portions of a process system. For example because it is the convergence point of many rich fluid inputs, the headbox of a papermaking process is often highly populated with microorganisms and may be expected to have a diversity index which varies widely over time. In contrast the treated fresh water that is used in the papermaking process is nearly organism free so a change in diversity and abundance there from a few organisms to an array of bacteria would indicate a problem. As a result sometimes noting the diversity index of a particular section affords insights that a system wide diversity index would not provide. Noting the kinds of changes in diversity and where they are located influences where the feed points for biocide should be located and how the population should be addressed.

In at least one embodiment the diversity index is used to preemptively avoid a harmful microbiological effect before it occurs. Because there are so many different sorts of organisms that correspond to specific problems in specific in commercial process systems it is sometimes efficient to focus on the presence or absence or the relative ratio of specific targeted organisms. For example some organisms are pioneers and some are adaptive biofilm-formers. A pioneer creates a biofilm or crustdeposit where there previously was none, while an adaptive biofilm-former exhibits resistance to a treatment program. If a review of the diversity index shows first the film or crust predominantly comprised one organism then later its composition changed to a different organism it could indicate the transition from a pioneer to an opportunistic adaptor and the biocide regimen can be modified to appropriately address this situation. Similarly if a primary film former tends to gain access to the system from one mechanism and the adaptive one from another mechanism properly identifying what kind of organism is present helps to identify the vector sources of the microbial contamination.

In at least one embodiment the diversity analysis can be used to focus quality control review of the end products. For example some organisms such as some fungi do not cause significantly impair the process itself but they form masses which tend to become embedded in end products or machine components and thereby cause unwanted defects, reduced felt dewatering and reduced mechanical efficiency. A rise in the concentration of fungi in the diversity index would suggest especially close scrutiny of the end product for defects is appropriate.

In at least one embodiment the nature of the change in the index is not as significant as the rate of the change in diversity. For example if a given diversity index over time tends to show a relatively static population diversity but it suddenly changes, this indicates that something significant has changed in the system. This could mean a material input may have a defect which stimulates population change, or a piece of equipment may be damaged or malfunctioning which opens up new niches for different organisms. As a result, diversity index analysis can be used to detect non-biological problems in process systems.

In at least one embodiment the change in diversity index can be used to detect a looming problem before it actually manifests. As previously mentioned a change in diversity index may indicate a defective material or damaged or malfunctioning equipment. Sometimes the change in diversity can be detected before other unwanted effects occur (such as loss of operational efficiency or defective end products) and identification of the cause of the change in diversity can moot a potential problem before its effects manifest in a significant or expensive manner. Similarly a change in diversity may indicate that crustdeposit or a biofilm or another organism induced problem will occur, but the index allows for the problematic microorganism to be removed before it causes its associated problems. Sometimes the rapid change indicates that a benign species which previously blocked the colonization efforts of a harmful organism is no longer potent and the harmful organism is now free to colonize that niche.

In at least one embodiment, the analysis of the diversity index occurs in a situation where the total cell count within the region analyzed remains unchanged but the composition of the microorganisms changes. In at least one embodiment, the change in diversity corresponds to a situation in which the total cell count increases or decreases.

In at least one embodiment, one or more portions of a process system are regularly sampled for their diversity index. The samples may be time indexed and may be correlated with other events at the facility such as the activation, deactivation, operating status, rate of production, and or temperature, of certain equipment, and/or the use of different materials, additives, or chemicals. This allows for the use of biological diversity as another means of quality control at the facility. A significant change in diversity that corresponds to some other event indicates that the other event may have some unexpected positive or negative impact on the process.

In at least one embodiment some microorganism induced effects are known to occur after a specific amount of time has elapsed from the moment of contamination. As a result a change in diversity index can be used to determine how long it takes for the organism to cause its associated problems. This method can be used both as a diagnostic (to find out how the organism functions) as well as a cost optimization tool. Cost optimization can be achieved by receiving advanced warning from the diversity change that a problem will occur within a given timeframe using the advanced warning to purchase or use of a remedy at a time when it has a lower cost or higher availability than it would if it was purchased as a sudden response to an unexpected emergency.

In at least one embodiment the diversity index can be used to detect spore-forming organisms. When these organisms are in spore form they have little or no metabolic activity and are highly resistant to biocides. It takes a large amount of biocide to control organisms once they are in the spore-state and the likelihood of spores making it into the finished product becomes very high. Dairyman's and liquid packaging standards are likely not to be met in a situation where spores are present. In contrast when these organisms are in a vegetative state they are susceptible to biocides and are much easier to control. Detection of spore-forming organisms by the diversity index method shifts the focus of the biocontrol program to prevention of the formation of spores.

In at least one embodiment the results of the diversity index analysis are used to augment the biocontrol program by determining how much, what kind, and how often, one or more biocide compositions are added to one or more locations within a commercial process system. In at least one embodiment any and all of the above and below embodiments are applied to a commercial system such as an industrial system including but not limited to a process water system, papermaking process, pulping process, food processing process, chemical refining process, wood processing process, water filtration process, water purification process, chemical synthesis process, coating processes, organic chemistry using processes, and any combination thereof. In at least one embodiment the diversity index is used to assess problematic microorganisms found in machine deposits, sheet defects, finished products, felts, etc. The method is based on analysis of nucleic acids in sample extracts.

In at least one embodiment the identification of the constituents of the diversity index is achieved through DNA based analysis involving the use of PCR primers to detect the presence, absence and quantity of microorganisms. U.S. Pat. No. 5,928,875 describes the use of PCR primers to detect the presence or absence of spore forming bacteria. In at least one embodiment the primer is targeted towards a part of a DNA strand which is highly conserved among a group of organisms. As a result, detecting the presence of that particular part of DNA is definitive proof of the presence a specific organism. PCR analysis is of particular use in analyzing felts and paper sheets due to the difficulty of correctly identifying its contaminating microorganisms because they lack viable organisms for traditional plating methods or ATP measurements.

In at least one embodiment the PCR analysis involves utilizing one or more of the methods described in the Article Primer Directed Enzymatic Amplification of DNA with a Thermostable DNA Polymerase, by Randall Saiki et al., Science, Volume 239, pp. 487-491 (1988). In at least one embodiment the PCR analysis involves utilizing one or more of the methods described in the Article Specific Synthesis of DNA in Vitro via a Polymerase-Catalyzed Chain Reaction, by Kary Mullis et al., Methods In Enzymology, Volume 155, pp. 335-350 (1987).

In at least one embodiment the PCR analysis is a qPCR analysis as described in Trade Brochure qPCR guide, prefaced by Jo Vandesompele, (as downloaded from website http://www.eurogentec.com/file-browser.html on Jan. 19, 2012). In at least one embodiment the method is a quantitative qPCR analysis. In at least one embodiment the method is a qualitative qPCR analysis.

In at least one embodiment, the polymerase chain reaction (PCR) is a method for targeting sequences of nucleic acid (DNA or RNA) and increasing the copy number of the target sequence to obtain useful quantities of nucleic acid for downstream analysis. This method can be applied to the detection of microorganisms in a variety of samples that include, but are not limited to, machine felts, sheet defects, machine deposits, etc.

In at least one embodiment, once DNA is extracted from the sample, using any of the DNA extraction kits available commercially, it can be analyzed in real-time using a PCR approach such as a Quantitative PCR approach. Quantitative PCR utilizes the same methodology as PCR, but it includes a real-time quantitative component. In this technique, primers are used to target a DNA sequence of interest based on the identity of the organism or function of a specific gene. Some form of detection such as fluorescence may be used to detect the resulting DNA or 'DNA amplicon'. The change in fluorescence is directly proportional to the quantity of target DNA. The number of cycles required to reach the pre-determined fluorescence threshold is compared to a standard that corresponds to the specific DNA target. A standard is typically the target gene that is pure and of known quantity at concentrations that span several logs. The number of copies of target DNA present in the sample is calculated using the standard curve. The copy number per sample is then used to determine the number of cells per sample.

In at least one embodiment a primer set is used which targets DNA sequences from bacteria using a conservative approach to quantify total bacteria. In at least one embodiment a primer set is used which targets primary biofilm-forming bacteria, including, but not limited to, *Meiothermus, Pseudoxanthomonas*, and *Deinococcus*. In at least one embodiment a primer set is used to target an adaptive biofilm-former which belongs to the Sphingomonadacea family of bacteria. In at least one embodiment the adaptive biofilm-former exhibited higher tolerance to oxidant-based biocontrol programs compared to other biofilm and planktonic microorganisms. In at least one embodiment the primer is used to distinguish between fungal and bacterial infestations.

In at least one embodiment the method involves distinguishing between DNA at the biological domain level. In at least one embodiment the method involves distinguishing between DNA of Bacteria, Archaea, and Eukaryota. These organisms have hugely differing DNA and a protocol which focuses on identifying the organism's DNA at the domain level is vastly simpler than more specific determinations. Because with felts, the organisms from different domains are often best treated differently, such a simple form of identification can be used to accurately identify the specific regimen best targeted to the particular contaminant. In at least one embodiment the test used is such that it would not distinguish between organisms of the same domain or between different kinds of Bacteria, or between different kinds of Archaea, or between different kinds of Eukaryota.

In at least one embodiment more than one primer is used to identify organisms that have more than one uniquely recognizable nucleotide sequence. In at least one embodiment the PCR analysis is used to detect genome sequences associated with enzymes unique to or nearly unique to specific organisms.

In at least one embodiment the method involves detecting a defect and then utilizing the PCR analysis to properly analyze the diversity index of the defect. In at least one embodiment the method determines if the defect is totally biologically based, totally non-biologically chemical based, or resulting from a combination of non-biologically chemical, mechanical, and biologically based sources. In at least one embodiment the defect is one or more plugs on a felt. In at least one embodiment the defect is a paper sheet having at least one or more of: a hole, a hole with a discolored halo around at least a portion of it, a streak of discoloration, a spot, a translucent spot, and any combination thereof.

In at least one embodiment a threshold level is methodology used to discount false positives. Sometimes PCR analysis detects traces of organisms that while present are not causes of a particular defect. In at least one embodiment the method involves discounting the presence of any organism detected at a concentration lower than a pre-determined level known for one or more particular organisms. In at least one embodiment the method involves discounting the presence of any organism detected at level lower than $10^4$ cells per gram (of the defect). In at least one embodiment the method involves discounting the presence of any organism detected at level lower than $10^4$ cells per ml.

In at least one embodiment the method is able to detect microorganisms that would not otherwise be detected by prior art methods. For example in cases where foulant is caused by an infestation of anaerobic or sulfate reducing organisms, methods such as ATP detection would not correctly identify the foulant source as biological as the amount of ATP produced by a microorganism under anaerobic conditions is significantly less than under aerobic conditions. Therefore the foulant source will be identified incorrectly and n chemical not an anti-biological approach would be used to attempt to resolve the problem. In another example, differentiation of microbial from chemical contamination in felts using traditional approaches such as plating, ATP detection, etc. is virtually impossible due to the fact that these samples dry out during transport and all viable organisms die. Utilizing the DNA approach would always correctly indicate a biological infestation because all life contains DNA.

The diversity index can use PCR such as but not limited to qPCR for the detection of total organisms such as bacteria; *Sphingomonas* species; *Erythrobacter* species; *Pseudomonas* species; *Burkholderia* species; *Haliscomenobacter* species; *Saprospira* species; *Schlegelella* species; *Leptothrix* species; *Sphaerotilus* natans; *Bacillus* species; *Anoxybacillus* species; members of the *Cytophaga-Flavobacterium-Bacteroides* phylum; green nonsulfur bacteria, including *Herpetosiphon*, members of the *Deinococcus-Thermus* phylum, including *Meiothermus* species; catalase-producing bacteria, amylase-producing bacteria, urease-producing bacteria, nitrifying bacteria, fungi, etc. These techniques utilize primers and standards pairs that allow for detection and quantification of target organisms based on conserved sequences. The primers target regions in the microbial genome that are highly conserved through evolution, while primers for specific phyla or genera target more variable regions of the genome.

Being able to accurately quantify an organism of interest present in a sample makes it possible to express that organism as a percentage of the total bacterial load in the sample. The diversity index can also be expressed quantitatively as the relative abundance of several target organisms. The diversity index for any part of a process can be measured at times when machines or processes are running well, thus creating a baseline. The diversity index measured at times of poor machine or process performance can then be compared to the baseline to look for fluctuations in microbial populations and to determine which bacterial groups are responsible for problems in the process. The diversity index can also be quantified for ease of comparison using the Shannon diversity index calculation to compare monitoring data among sample locations or relative to a baseline. Treatment strategies and feed points can then be altered accordingly to combat the problem.

A diversity index based on quantification of DNA measures the presence and diversity of organisms in a process, independent of their viability. Ribonucleic acid (RNA), specifically messenger RNA (mRNA), is a molecule that is produced only by living organisms, and has properties such that, depending on the target, are unique to a specific phylum or genera of bacteria. By amplifying mRNA sequences that are unique to the organisms listed above it becomes possible to determine which bacteria are present in their viable form. Accurate detection of viable organisms can then be used as a tool for assessing the efficacy of treatment strategies of process waters. This can be accomplished by comparison of the diversity index to the viability index.

This method would quantify the amount and type of viable bacteria present in process samples. The quantitative (real time) polymerase chain reaction method can be applied to detect messenger ribosomal nucleic acids (mRNA). mRNA is transcribed DNA that is sent to the ribosome to serve as a blueprint for protein synthesis in a process known as translation. mRNA is produced only by living cells. RNA from living cells can be isolated with the use of commercially available kits. Detection of mRNA requires an extra step in the quantitative polymerase chain reaction. Reverse transcriptase is added to the reaction cocktail to transcribe mRNA into its complementary DNA (cDNA). Two sets of primers are required for this experiment. The first targets specific mRNA, while the second is used to amplify the resulting cDNA produced by the reverse transcriptase reaction.

EXAMPLES

The foregoing may be better understood by reference to the following examples, which are presented for purposes of illustration and are not intended to limit the scope of the invention.

Example #1

A coated free sheet mill experienced persistent deposition in one of the machine headboxes, which was believed to be the cause of defects in the final product. The headbox itself suffered from an accumulation of chemical deposits and fibrous growths. Microscopic and chemical analysis showed little to no bacterial presence within the accumulation. Microorganisms were assumed to be the underlying cause of the problem. However, traditional monitoring techniques (e.g. standard plate counts and ATP levels) used to analyze process samples did not indicate elevated levels of microbial activity. Specifically the results indicated no more than 100 CFU/ml and no more than 100 RLU (ATP).

Deposit samples from the headbox were analyzed over the course of several months using qPCR techniques to develop a diversity index. Initial qPCR results from the analysis of headbox deposits exhibited high levels of microbial loading, as well as elevated densities of pioneering and adaptor biofilm-formers (FIG. 1). The treatment strategy was augmented with the addition of biocides to both the pulper and the broke silo. The feed rate of the oxidant-based biocontrol program was also increased. Analysis of deposits collected one month later detected little change in the total bacterial load of the headbox deposits (FIG. 1A). The number of pioneering biofilm-formers decreased one-log, while the density of adaptive biofilm-formers decreased four-logs (FIGS. 1B and 1C). The amount of headbox deposits and frequency of sheet defects continued to remain unchanged. Traditional plating and ATP analysis of the stock and process water system indicated little biological activity. The ATP and plate count values were averaging less than 100 RLU and 100 colony-forming units per gram (CFU/g), respectively.

The treatment strategy was further optimized through the addition of unstabilized chlorine and biocides to the broke silo and the pulper. After implementation of the last set of changes, additional samples were collected and analyzed. The total bacterial load of the deposit showed a decrease of nearly one-log (FIG. 1A). The final set of deposit samples showed a decrease of nearly two-logs in the density of primary biofilm-formers (FIG. 1B). Adaptive biofilm-formers remained at near-background levels (FIG. 1C). Again, despite improved control of the microbial population, the defect frequency, the nature of the defects, and headbox deposition remained unchanged.

Figure 2:
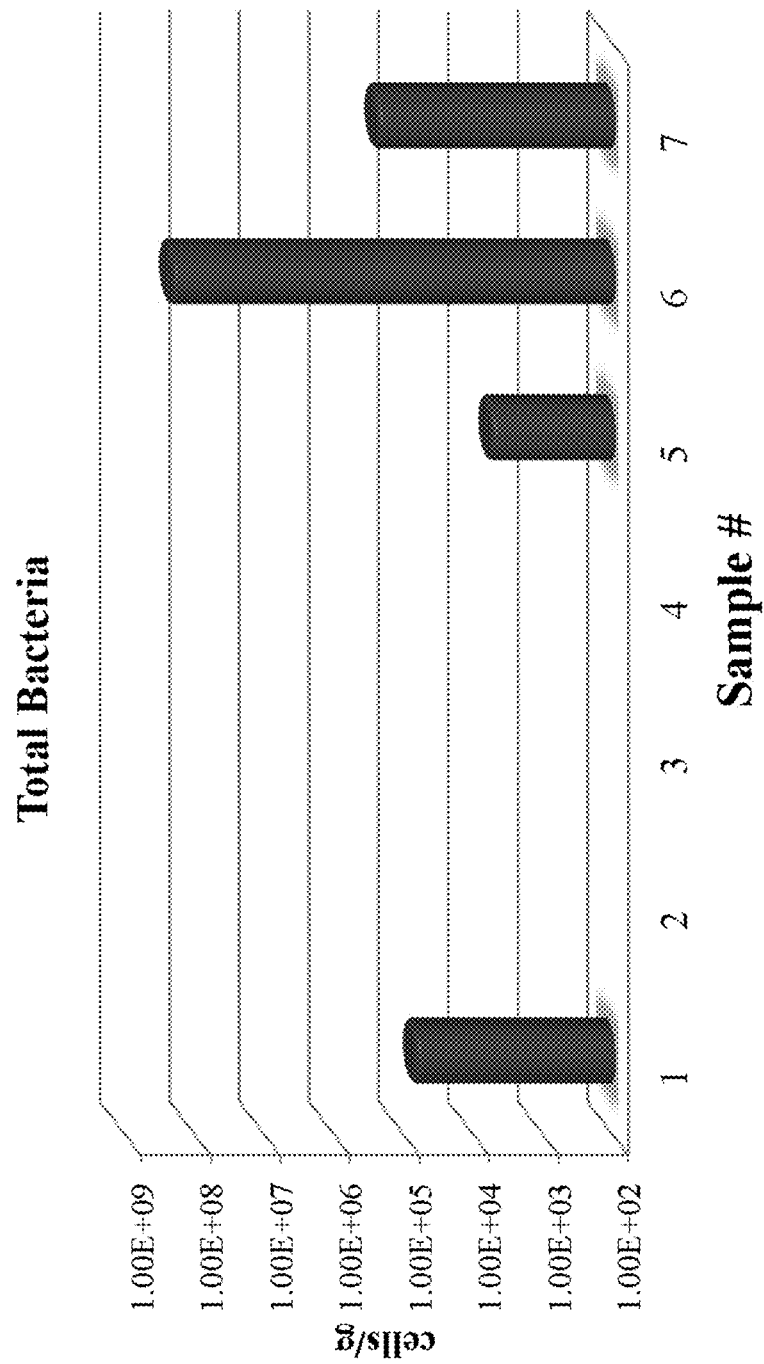

Sheet defects from this mill were analyzed using the same qPCR-based approach. It is impossible to determine bacterial content in defects using traditional plating and ATP methods because many of the bacteria that may have been present in the defect are killed by the high temperatures of the dryer section. Chemical analysis does not provide a definitive answer about bacteria present in the sheet as it relies on ninhydrin staining. This approach is non-specific and prone to false positive and false negative results. DNA analysis of holes and sheet defects from this mill detected very low bacterial density (FIG. 2, Samples 1-5). Primary and adaptive biofilm-formers were not detected in the sheet defects analyzed from this mill. Therefore, bacterial slime was not likely contributing to defects and quality issues at this mill. In comparison, a mill suffering from significant biological deposition had defects containing much higher microbial loading (FIG. 2, Sample 6). Furthermore, similar bacterial species were identified in the deposits and defects. Ninhydrin staining of these defects did result in a positive reaction indicating the presence of microorganisms. In another case, bacteria were detected in sheet defects at levels just above the minimum density required to be considered a biological defect. However, the ninhydrin reaction was negative indicating the defect did not contain microorganisms (FIG. 2, Sample 7). Quantitative qPCR examination of headbox deposits demonstrated reductions in both primary and adaptive biofilm-formers following each modification to the treatment strategy. The fact that there was a drastic decrease in these target organisms and no decrease in the amount of deposition or defect frequency, indicates that bacteria are likely not responsible for defect problems in this machine system. Primary biofilm-formers colonize machine surfaces and create a favorable environment for attachment and proliferation of other organism types. Without the presence of these organisms, bacteria may attach to machine surfaces following the deposition of chemical debris that can serve as a good growth medium. It is likely that chemical additives and fiber were depositing inside the headbox, resulting in a microenvironment suitable for microbial colonization. Since the analysis of sheet defects revealed negligent microbial presence, microorganisms were ruled out as the primary source of deposition in the headbox and adverse effects on product quality. Efforts to improve machine performance were focused away from biocontrol and toward better mechanical control of the system allowing for improved operational conditions and product quality.

Example #2

A coated free sheet mill utilized a competitive oxidant-based biocontrol program for several years. Control of microbial growth was perceived as adequate; however, there was an opportunity to further reduce sheet breaks for improved process efficiency. The program was implemented and optimized in several phases. Bacterial density throughout the process remained low and a reduction in sheet breaks was documented. The average number of breaks per day decreased from an average of 1.2 breaks per day to 0.42 breaks per clay.

Figure 3:
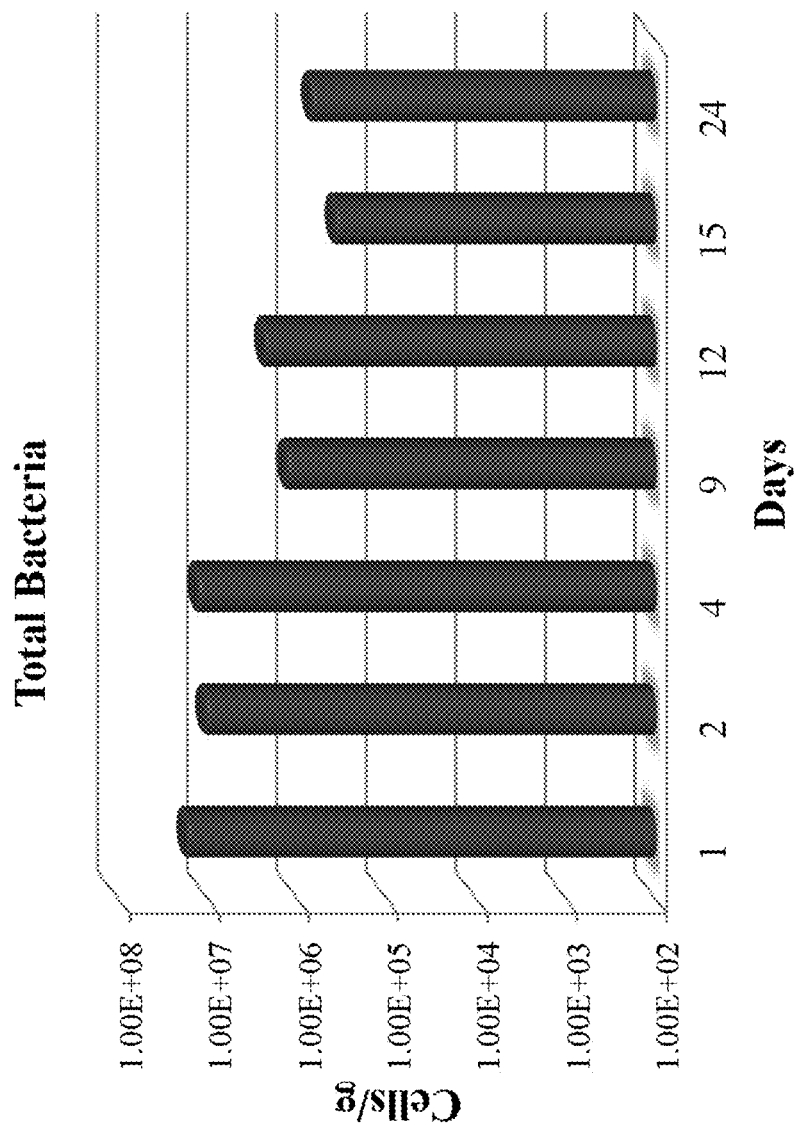

Approximately two-years after the implementation of the optimized program, it was observed that process conditions had become more variable and increasing concentrations of biocontrol products were required to maintain the same level of control. A system survey using traditional monitoring tools such as plate counts and ATP measurements, indicated that bacterial density in the process water system remained low and no or little increase was observed in the headbox and broke system. However, the mill was suffering a severe outbreak of holes and defects. While traditional monitoring techniques indicated no change in the performance of the biocontrol program, the on-line activity monitor detected increasing microbial activity (FIG. 3).

A diversity index analysis utilizing qPCR analysis of the machine deposits and sheet defects all confirmed the presence of pioneering and adaptive biofilm-formers. The density of total bacteria in the defects was approximately $1.8 \times 10^7$ cells per gram (FIG. 3). This evidence indicates the role of microorganisms in the defect and quality issues. The machine underwent a caustic boilout after which, the online activity monitor demonstrated a reduction in microbial activity and a more stable ORP value indicating improved program performance and resilience. The amount of microorganisms in sheet defects decreased from $10^7$ to $10^5$ cells/g following the boilout (FIG. 3). This confirms that qPCR can detect microbial contribution to sheet defects which cannot be detected using traditional techniques. In addition, qPCR can be used to assess the efficacy of the biocontrol program on the final product.

Example #3

Figure 4:
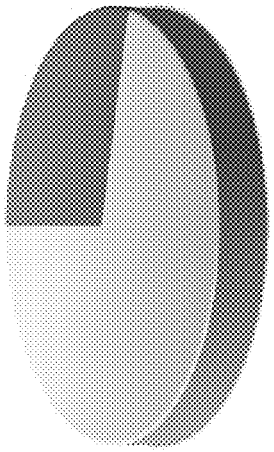
FIG. 4 illustrates pie charts denoting microbial diversity in DNA samples collected from machine felts from three different paper mills.
Figure 4:
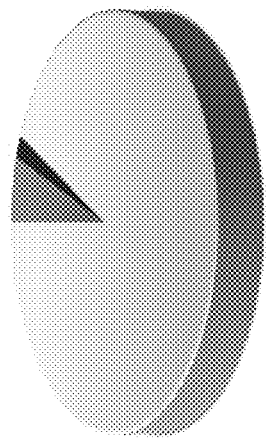
Figure 4:
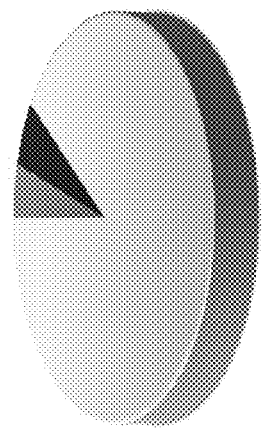

Felt samples from two paper mills that were experiencing performance issues, which manifested themselves as on-machine deposits and sheet defects, were analyzed using qPCR. Each sample was tested for the presence of microorganisms. Once it was determined that each sample contained high amounts of bacteria, the samples were then analyzed for the presence of adaptive and primary biofilm-formers, which included Sphingomonadaceae fm., *Meiothermus, Geothermus*, and *Pseudoxanthomonas* which have been known to contribute to problems with machine efficiency and product quality. Both mills contained normal levels of adaptive biofilm-formers, however, Mill 1 had twice as many primary biofilm formers as Mill 2 (FIG. 4). The level of adaptive biofilm formers was determined to be normal as its levels were in the range that indicated it is likely not contributing to the problem. Diversity index showed that the level of pioneer biofilm-formers at Mill 2 was at a near-background level. High levels of pioneer biofilm-formers at Mill 2 suggested biofilm formation in felts which leads to felt plugging and reduced water removal from the sheet. The presence of biofilm on the felts can lead to increased deposition of other matter which can then redeposit onto the sheet. Elevated levels of pioneer biofilm-formers at Mill 1 suggested that additional analysis of other parts of the process such as shower water, additives, storage chests, etc. were needed to determine where these organisms were originating.

The result of these examples demonstrates that conventional plating techniques and oxidant residuals may indicate adequate biocide dosing and control of microbial growth, while deposition, defects and breaks remain prevalent. Utilizing a diversity index comprising PCR and qPCR methods provides more accurate information regarding microbial growth and biofilm formation in industrial water systems.

These strategies allow for rapid analysis of the contribution of microorganisms to deposit formation and can be used to rapidly determine whether or not deposits containing microorganisms are contributing to defects.

A qPCR based diversity index allows for rapid analysis of sheet defects to determine the contribution of microorganisms to quality issues. This new approach has been demonstrated to allow for a more proactive diagnosis of problems leading to improved machine efficiency and product quality.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and/or incorporated herein. In addition the invention encompasses any possible combination that also specifically excludes any one or some of the various embodiments described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of addressing a microorganism infestation in an industrial process system, the method comprising the steps of:
   taking at least one first measurement which identifies the relative concentration of two or more organisms present in at least one portion of the industrial process system,
   taking at least one second measurement which identifies the relative concentration of two or more organisms present in the at least one portion of the industrial process system, the identifications at least partially defining a subsequent diversity index, the at least one second measurement taken later than the first measurement(s),
   noting any relative change in concentration of the two organisms,
   if the relative concentration of one of the measured organisms exceeds a pre-determined threshold amount, determining if the change is associated with an unwanted effect on the industrial process system, and
   implementing a remedy to remediate the unwanted effect wherein regardless of the identity of the at least one organisms, if their relative concentrations increase relative to the prior measurement by an amount more than the threshold even if the overall biological population remains the same, a biocide treatment is added to the system.

2. The method of claim 1 in which the first and second measurement are performed by at least one item selected from the list consisting of DNA analysis, PCR analysis, qPCR analysis, and any combination thereof.

3. The method of claim 1 in which the threshold amount is $10^4$ cells per ml of fluid taken from the system or $10^4$ cells per gram of an end product of the industrial process or of a solid sample from the industrial process.

4. The method of claim 1 further comprising the step of identifying if one of the organisms is a pioneer and if one is an adaptor, if one is a pioneer and its concentration increases by more than the threshold in the subsequent index, the remediation includes applying a biocide regimen targeting the pioneer, if no pioneer formers are detected the remediation includes identifying and eliminating a non-biological vector which facilitates the settlement of the microorganisms.

5. The method of claim 1 further comprising the step of identifying if one of the organisms is a pioneer and if one is an opportunist, if one is a pioneer and its concentration increases by more than the threshold in the subsequent index, the remediation includes applying a biocide regimen targeting the pioneer, if no pioneers are detected the remediation includes identifying and eliminating a non-biological vector which facilitates the settlement of the microorganisms.

6. The method of claim 1 further comprising the step of correlating the change in diversity index to another event that occurred in the industrial system, the other event selected from the list consisting of: changing the source of at least one feed material, changing the kind of at least one feed material, changing the rate of operating at least a portion of the system, and any combination thereof, and reversing the event.

7. The method of claim 1 in which the overall concentration of cells in the sample remains unchanged between the first and second measurements.

8. The method of claim 1 in which the measurements are taken in a portion of system that a deposit has formed on and the deposit does not contain any significant biological component.

9. The method of claim 1 in which the measurements are taken in over a plurality of locations throughout the system and the indices compare overall system populations.

10. The method of claim 1 in which at least one third diversity index measurement is taken subsequent to the second measurement and subsequent to the remediation and the efficacy of the remediation is evaluated by the change in the relative concentrations of the at least two organisms as measured in the third diversity index measurement.

11. The method of claim 1 in which the overall concentration of cells in the sample remains unchanged between the first and second measurements, the identity of the first and second organisms are not known to cause any unwanted effects on the process equipment or end product, and an effective biocide is added to the system to kill the first and second organisms when a threshold change is detected.

12. The method of claim 1 in which one of the organisms is capable of forming spores which are resistant to biocides and when the relative amount of that organism grows in excess of the threshold, treatment is targeted to the area of the process with vegetative cells to prevent sporulation.

13. A method of addressing a microorganism infestation in an industrial process system, the method comprising the steps of:
  taking at least one first measurement which identifies the relative concentration of at least one organism present in at least one portion of the industrial process system,
  determining if the concentration of the at least one organism exceeds a predetermined threshold for that organism,
  if exceeding, determining if the threshold exceeding organism is an adaptor or is an pioneer,
  if an adaptor implement a remedial strategy which takes into account the organism's resistance to biocides,
  if a pioneer implement a remedial strategy which utilizes a lower dosage of biocide than if the organism were an adaptor.

14. The method of claim 13 in which a measurement is also taken determining the absolute population of all microorganisms infesting the industrial process system, and
  determining if the concentration of the at least one organism exceeds a predetermined threshold for that organism relative to the overall population of microorganisms,
  if exceeding, determining if the threshold exceeding organism is an adaptor or is an pioneer,
  if an adaptor implement a remedial strategy which takes into account the organism's resistance to biocides,
  if a pioneer implement a remedial strategy which utilizes a lower dosage of biocide than if the organism were an adaptor.

15. A method of addressing a microorganism infestation in an industrial process system, the method comprising the steps of:
  taking at least one first measurement which identifies the relative concentration of two or more organisms present in at least one portion of the industrial process system,
  taking at least one second measurement which identifies the relative concentration of two or more organisms present in the at least one portion of the industrial process system, the identifications at least partially defining a subsequent diversity index, the at least one second measurement taken later than the first measurement(s),
  noting any relative change in concentration of the two organisms,
  if the relative concentration of one of the measured organisms exceeds a pre-determined threshold amount, determining if the change is associated with an unwanted effect on the industrial process system, and
  implementing a remedy to remediate the unwanted effect;
  the method further comprising the step of correlating the change in diversity index to another event that occurred in the industrial system, the other event selected from the list consisting of: changing the source of at least one feed material, changing the kind of at least one feed material, changing the rate of operating at least a portion of the system, and any combination thereof, and reversing the event.

* * * * *